(12) United States Patent
Kagermeier et al.

(10) Patent No.: US 7,343,189 B2
(45) Date of Patent: Mar. 11, 2008

(54) METHOD AND DEVICE FOR PLACING A PATIENT REPEATEDLY INTO THE SAME RELATIVE POSITION

(75) Inventors: Robert Kagermeier, Nürnberg (DE);
Uwe Urmoneit, Gerhardshofen (DE);
Donal Medlar, Weisendorf (DE)

(73) Assignee: Siemens Aktiengesellschaft (DE)

( * ) Notice: Subject to any disclaimer, the term of this patent is extended or adjusted under 35 U.S.C. 154(b) by 539 days.

(21) Appl. No.: 10/384,204

(22) Filed: Mar. 6, 2003

(65) Prior Publication Data
US 2003/0225325 A1 Dec. 4, 2003

(30) Foreign Application Priority Data
Mar. 7, 2002 (DE) .............................. 102 10 050

(51) Int. Cl.
*A61B 5/05* (2006.01)
(52) U.S. Cl. ............... 600/407; 382/128; 382/131; 382/132; 382/294; 378/8; 378/20; 378/65; 378/95
(58) Field of Classification Search ........... 600/407, 600/410, 411, 414, 417, 424, 426, 429; 606/130; 382/128, 131, 132, 294; 378/8, 20, 65, 95
See application file for complete search history.

(56) References Cited

U.S. PATENT DOCUMENTS

| | | | |
|---|---|---|---|
| 5,222,499 A * | 6/1993 | Allen et al. ............... 600/426 |
| 5,558,091 A * | 9/1996 | Acker et al. ............... 600/424 |
| 5,590,655 A * | 1/1997 | Hussman ................. 600/426 |
| 5,628,315 A | 5/1997 | Vilsmeier et al. |
| 5,662,111 A | 9/1997 | Cosman |
| 5,820,553 A | 10/1998 | Hughes |
| 6,016,439 A * | 1/2000 | Acker .................... 600/411 |
| 6,279,579 B1 | 8/2001 | Riaziat et al. |
| 6,405,072 B1 | 6/2002 | Cosman |
| 6,728,424 B1 * | 4/2004 | Zhu et al. ............... 382/294 |
| 6,937,696 B1 * | 8/2005 | Mostafavi ................ 378/95 |
| 2002/0177770 A1 * | 11/2002 | Lang et al. .............. 600/410 |

FOREIGN PATENT DOCUMENTS

| | | |
|---|---|---|
| DE | 343644 A1 | 4/1986 |
| DE | 19728788 A1 | 1/1999 |
| DE | 196 21 612 C2 | 3/2001 |
| DE | 199 53 177 | 6/2001 |
| DE | 101 27 235 A1 | 11/2002 |
| EP | 0 840 253 A2 | 10/1997 |
| GB | 2340716 A | 8/1998 |
| WO | WO 98/04194 | 2/1998 |
| WO | WO 99/27839 | 6/1999 |
| WO | WO 00/04467 | 1/2000 |

* cited by examiner

*Primary Examiner*—Eleni Mantis Mercader
*Assistant Examiner*—Baisakhi Roy
(74) *Attorney, Agent, or Firm*—Brinks Hofer Gilson & Lione (57) ABSTRACT

The invention relates to a method for repositioning a patient in a diagnostic/therapeutic system, as well as to such a system, wherein a repeated, accurate repositioning is achieved by producing difference images from a reference image and a current image, each in two recording axes, which are independent of each other, and by subsequently minimizing the visible differences. The reference images are produced with the same camera setting as the current images.

25 Claims, 5 Drawing Sheets

METHOD AND DEVICE FOR PLACING A PATIENT REPEATEDLY INTO THE SAME RELATIVE POSITION

REFERENCE TO RELATED APPLICATIONS

The present patent document claims priority to German Application Serial No. DE 10210050.0, filed Mar. 7, 2002, which is hereby incorporated by reference.

FIELD

The invention relates to a method for the repeated placement of a patient into the same position in relation to the coordinate system of an imaging diagnostic and/or radiation-therapeutic system. The invention further relates to an imaging diagnostic and/or radiation-therapeutic system with a positioning device for the relative positioning of a patient and the system, having at least one camera, preferably in the visible and/or infrared wavelength range, for providing an image and for checking the position of a patient to be treated, having a memory device for storing the images, and having a reproducing device for displaying these images.

BACKGROUND

In the course of the repeated production of diagnostic images, for example in connection with X-ray photography, computer tomography, magnetic resistance tomography, ultrasound tomography or positron-emitting tomography, but also in connection with therapeutic, in particular radiation-therapeutic systems, it is necessary to achieve a positioning of the patient in a repeated procedure, which is as accurate as possible in relation to the coordinate system of the respective system for checking the ongoing process, or for the optimal treatment of the respective area of the body.

In this connection, it is known to apply markings to the patient, which are compared with reference points in the system, wherein the patient and the system can be displaced in such a way that these markings are each brought into congruence with a reference system of the device. Reference is made to the Laid-Open, Non-Examined Patent Application DE-OS 44 32 890 and to U.S. Pat. No. 6,279,579 in regard to such a system and such a method.

The problem with these known methods and devices lies in that in case of repeated treatments, the respective markings must be reapplied to the patient, since it is actually not possible to provide the patient with permanent markings or visible lesions which remain unchanged over a long period of time.

The reapplication of such markings is prone to errors which in actual use result in that repositioning of the patients is located within a range of 5 to 8 mm of reproduction accuracy, with occasionally greater deviations of up to 10 mm.

OBJECT AND SUMMARY

It is therefore the object to find a simple method and a simple device which permit the repeated positioning of a patient in a diagnostic or therapeutic system, whose reproducibility is considerably better than the above mentioned 5 to 8 mm reproduction accuracy.

The inventors have found that it is possible to considerably improve the accuracy of positioning a patient in a diagnostic or therapeutic system during repeated positioning if, the position of the patient in the first session is stored by means of producing images in two planes which are independent of each other, or two axes, which are independent of each other. In the course of a repetition of the positioning of this patient in the same position in the coordinate system of the same system, or a different system, a comparison is made of the originally obtained reference images with current images taken by means of a camera, or several cameras with the identical camera settings, in particular the same positional orientation, the identical perspective and/or the same recording axis. If, in the process, the originally filed reference images are superimposed on the currently produced images, the difference between the original positioning and the now current position of the patient becomes visible.

In this connection, the subtraction method, known per se, has been shown to be particularly advantageous, wherein the current image is subtracted pixel by pixel from a background image, in this case the reference image, so that the difference between the two images become very clearly visible in the difference image resulting from this operation. If such an image is placed on the monitor used by the operator of such a system, it is very easy for him to displace the patient until an optimal congruence between the original position of the patient during the first session and the now current position exists.

Such a method for positioning a patient can be automated in a simple way. For example, the features of the method, known per se, for detecting the movement of objects as known from Published, Non-Examined Patent Application DE-OS 196 21 612 B2, for example, can be used. Here it is merely necessary to interpret the detected movement of an object in two images in such a way that, for creating a congruence of the current position of a patient with an original reference position, this detected "movement" is canceled in that an appropriate control correspondingly acts on a positioning device for the patient.

To optimally reposition the patient in three-dimensional space, it is useful to compare images in at least two axes, which are independent of each other or not parallel, preferably orthogonal axes, with originally made reference images with the same camera setting.

In accordance with an additional aspect, there is also the possibility, besides the exact repositioning of a patient, to achieve an improved correlation between diagnostic images, preferably tomograms, of an imaging system, such as a computer tomograph, for example, and the current position of a patient with this method. To this end, the visual reference images are brought into correlation with the original diagnostic images, preferably tomograms, and thereafter this correlation is transferred to a therapeutic system, so that in the therapeutic system it is now possible to achieve a substantially more accurate treatment of sick areas of the body. It is assured, for example in connection with the use of radiation therapy with ionizing radiation, that a sufficiently high dose is administered to sick areas, while the surrounding healthy areas are subjected to a substantially lesser radiation stress and are therefore not, or only slightly damaged. The procedures required for this are generally known, however, success depends on an accurate positioning of the area to be treated.

Based on the experience of the inventors laid out above, they propose to improve the method, known per se, for the repeated identical relative positioning of a patient in the coordinate system of an image-providing diagnostic and/or radiation-therapeutic system in such a way that, in a first session, at least two reference images in at least two different camera positions and with different recording axes are made of a patient or an area of the patient, and are stored. During each subsequent session, current images are taken with the same camera setting, i.e. in particular identical camera position, perspective and recording axis, wherein at least two images are overlaid with previous reference images in such a way that the differences between the images become apparent. Thereafter, the position of the patient in relation to the system can be changed until the differences between the reference images and the images which are current for the new position of the patient have been minimized.

A video installation, which compares difference images from the current video camera with the reference images from the initial session by means of correspondingly rapid and effective calculating processes is particularly suited for the above described method.

In this connection, it should be pointed out that it is possible to use camera settings with different focus, however, under normal conditions it is necessary to obtain the same perspective.

Besides a visual check of the superimposed images or difference images on a control monitor, it is also possible to display purely computerized information regarding the differences between the reference images and the current images in a numerical or otherwise adequate form.

The subtraction method, known per se, has been shown to be particularly advantageous for representing the differences between the reference image and the current image, which is known, for example, for the automatic detection of movements by video systems for monitoring rooms. Besides this subtraction method, there is also the possibility of using an addition method or a mixed method, which emphasizes the differences in the images.

There is also the possibility of emphasizing the calculated differences in the images in color and to mix them in with the current images. If a particularly exact positioning is to be performed, it is also possible to represent individual partial areas in enlargement, so that smaller differences can also be detected particularly well on the monitor by the operators.

A further possibility of showing the differences between the reference images and the current images more strongly consists in an additional image processing of the reference images and the current images, for example by increasing the gradation or by an emphasis of the contours.

According to the further conceptualization by the inventors, they also propose that the position and/or perspective of the camera and/or the recording axis in relation to the imaging diagnostic and/or therapeutic system is stored in at least one reference image, and that prior to taking current images, the at least one camera is aligned in accordance with the stored data. It becomes possible to transmit the reference images between various devices so that it becomes possible, for example, to better compare images of a patient taken by means of X-ray computer tomography with images taken by means of another image-producing method, for example an MRI. In this connection, arbitrary combinations of known diagnostic imaging devices are possible.

The inventors furthermore propose to expand the method in such a way that the reference images of the first system are brought into spatial correlation with diagnostic tomograms of this system, and that in the second system, the spatial correlation of the diagnostic tomograms in relation to the current image is reestablished in order to improve the positioning of the patient in the radiation-therapeutic system and to treat the location of the illness more directly.

Advantageously, there is furthermore the possibility to transmit the produced reference images, including the camera settings correlated with them, to a further system by means of a remote data connection, wherein the at least one camera, preferably two cameras, of the further system are adjusted in accordance with the transmitted camera settings from the first system.

The inventors also propose, besides the method, to further develop the image-providing diagnostic and/or therapeutic system, known per se, having a positioning device for the relative positioning of a patient within the coordinate system of the system, having at least one camera, preferably in the visible and/or infrared wavelength range, for making an image and checking the position of a patient to be treated, having a memory for storing the images and having reproducing device for displaying these images, in such a way that device for producing at least two images in the visible and/or infrared wavelength range in at least two independent recording axes, and device for the electronic storage of the images, are provided. The system should additionally be expanded by a device for comparing currently taken images with reference images taken in a previous session and stored, and a device for displaying the difference between the reference images and the current images should be provided.

By a diagnostic or therapeutic system designed in this way, it is now possible to execute the previously explained method and to achieve an improved repositioning of the position of the patient in the coordinate system of the system, because on the basis of the at least two images, the operators are now capable of detecting deviations of the current position of the patient in relation to a previously defined reference position, and to move the patient until the differences between the current images and the reference images are reduced to a minimum.

By way of amplification, the above mentioned coordinate systems of the system do not necessarily have to be stationary coordinate systems, which are identical with the portion of the therapeutic or diagnostic system connected to the building, but can also be the coordinate system of the imaging device, or the coordinate system of the therapeutically operating portion of a radiation source.

Although it is quite possible to produce the means for comparing the current images with the reference images solely on a hardware basis, it is advantageous to provide a computer system with a computer program for this, which performs the method steps of the method and represents image differences on a monitor.

A further advantageous embodiment of the system can provide a transmitting and/or receiving device for use in a data net for the transmission of images and, if required, their camera settings. It becomes possible to transmit a reference position of a patient obtained in a first system in a simple manner to the second system. For example, a direct data connection can be established for this, or the transmission can take place via the Internet, preferably with appropriate safety precautions.

The above mentioned possibility is basically a complete transmission of the reference images taken and, if required, camera settings wherein, however, there are also methods available for comparing two similar data sets via a data net connection, without the complete data sets needing to be stored on a single computer. Reference regarding this method is made to International Patent Application WO 00/04467, whose entire disclosure regarding the comparison of two data sets via a network connection of which is incorporated herein by reference. A system and a method is presented in this application, by means of which it is possible to compare two similar data sets, for example a reference image and a current image, "online" on two computers located remotely from each other and connected by a data link, without it being necessary to exchange the entire data sets between the computers. An additional security aspect is provided by this type of data transmission, since no complete digitized images are being transmitted via the data net, so that, without having access to the reference data set, there is no possibility of recognizing the actual images by means of the unauthorized tapping of such a connection.

In a further advantageous embodiment of the system, the inventors propose that at least one camera for generating the reference images and/or the current images is arranged so that it is movable, preferably automatically controlled, in space and/or orientation. The possibility of being able to freely adapt to the conditions and the camera settings for reference images is provided this variability of a system, so that the highest possible compatibility between different diagnostic and therapeutic systems can be achieved.

The inventors suggest that preferably at least two cameras should be available, which simultaneously produce the reference images and/or the current images at different camera settings, wherein they are arranged in axes which are independent of each other or not parallel, preferably orthogonally in respect to each other.

Additional features and advantages of the invention ensue from the following description of preferred embodiments, making reference to the drawings. The exemplary embodiments will be explained in greater detail in what follows.

DETAILED DESCRIPTION OF THE PREFERRED EMBODIMENTS

Figure 1:
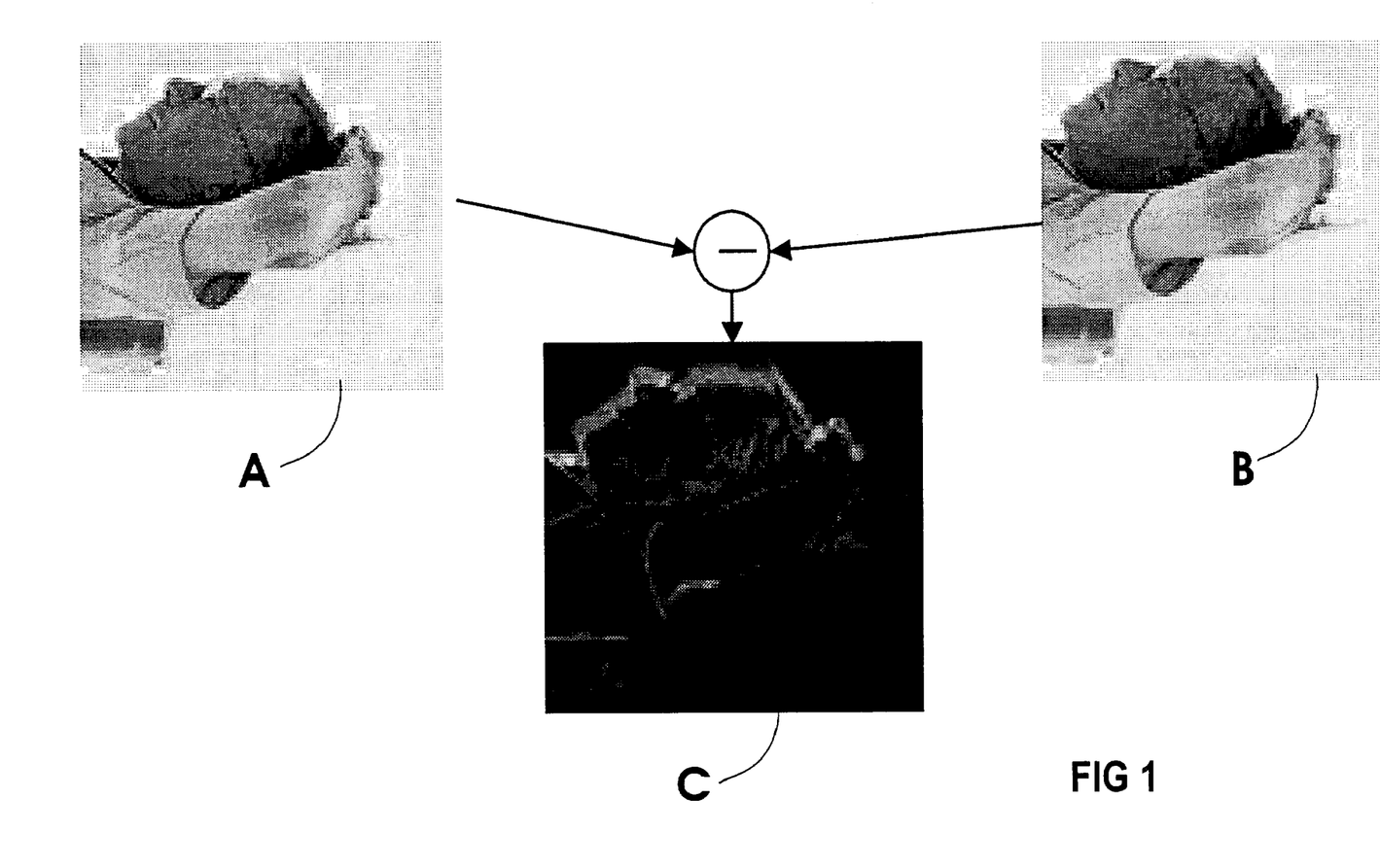
FIG. 1 represents a subtraction method of two visual images of a patient in different positions, and the subtraction image resulting therefrom.

The basic principle of the method for the repeated positioning of a patient in a system is represented in FIG. 1. The image A shows a patient in a first reference position, such as was taken by a video camera of a computer tomograph, for example.

Image B shows the same patient in the same system, taken at an identical camera position, perspective and recording axis, however, there is a difference in the position of the patient in the coordinate system of the computer tomograph from the original image. Both images are superimposed over each other in an image processing system, wherein a subtraction method is used here, wherein the image information from the image A is subtracted pixel by pixel from the image information from the image B, so that the result is the image C represented in the center. If the images A and B are identical images, i.e. the patient is in the identical position in the provided camera setting, a black homogeneous surface results in the image C. However, if the two images A and B differ, the differences are emphasized by light shadings, as shown in this example. It can be clearly seen in the represented image that the head of the patient takes up a higher position in the second image B than in the first image, so that the contour of the face in the front area stands out as a light shadow.

The images in the transverse axis represented in FIG. 1 emphasize displacements in the longitudinal body axis, while images in the sagittal direction, or in the longitudinal axis of the body, permit positioning in the longitudinal axis and the transverse axis of the patient.

The smallest deviations from a position first defined in a reference image A can be well recognized in this way and can therefore also be corrected.

Figure 2:
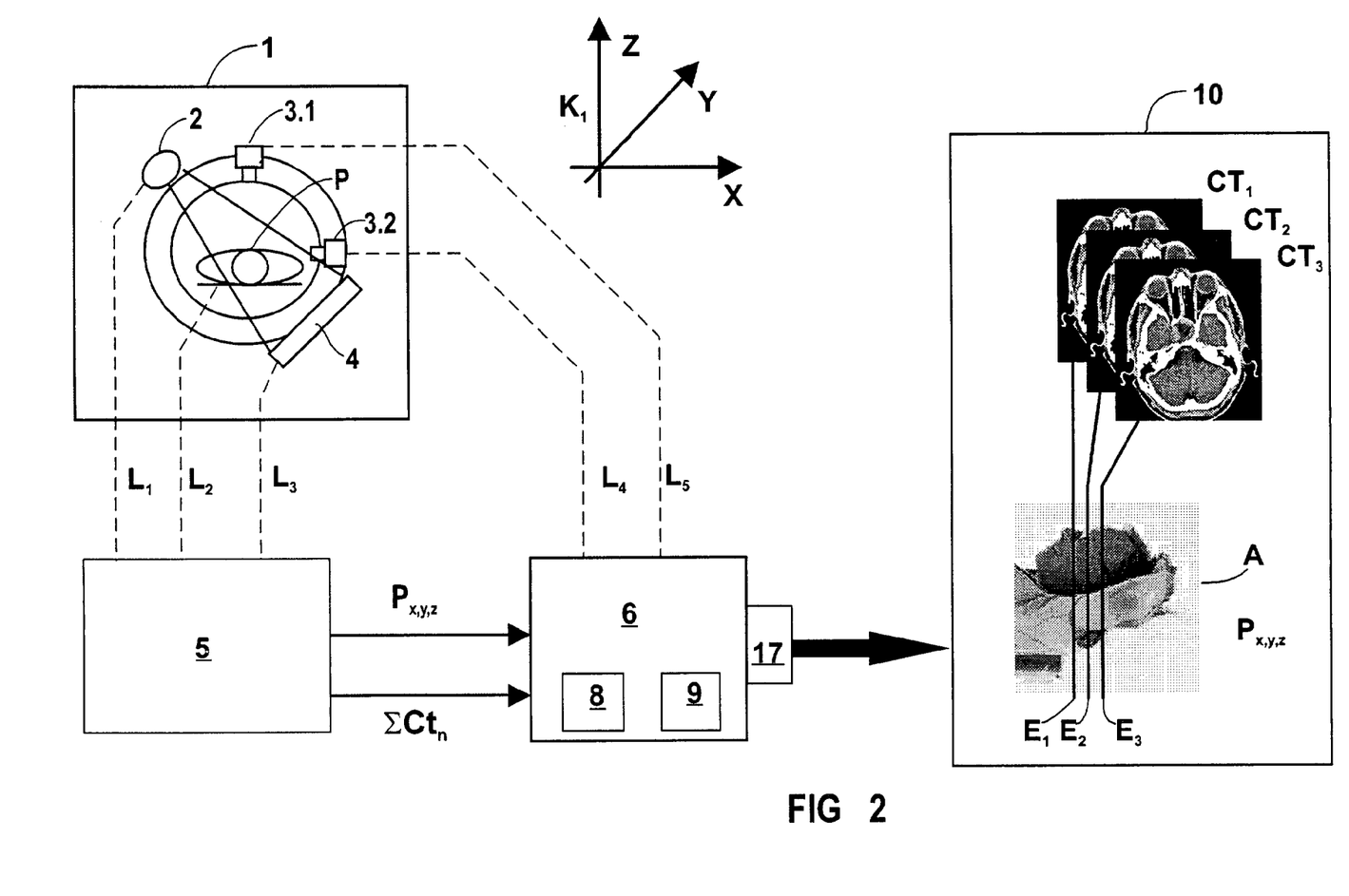
FIG. 2 shows a computer tomograph (CT) with two cameras for producing a reference image.

A computer tomograph is represented in FIG. 2 and is equipped in a known manner with an X-ray tube 2 and a detector 4, which produce tomograms $CT_1$ to $CT_n$ of a patient P. In addition, the CT has two video cameras 3.1 and 3.2, which are arranged in the Z- and X-axes of the coordinate system $K_1$ of the CT. The X-ray tube 2 and the detector 4 are connected with a CT control image computer via the lines $L_1$ and $L_3$, while the positioning of the patient P can also be performed with the aid of the computer unit 5 via the line $L_2$. The positional data $P_{x, y, z}$ determined by the computer 5, as well as the CT image information $CT_n$, are transmitted to the video recording system 6. The video recording system 6 furthermore contains the image information from the two video cameras 3.1 and 3.2 in the axes Z and X. In this way, it is possible for the video recording system to provide a correlation between the calculated CT tomograms $CT_1$ to $CT_n$, in relation to the visual images in the planes $E_1$ to $E_n$.

For reasons of clarity, only the recording by the camera 3.2 with the corresponding video image A is represented in FIG. 2. Three planes $E_1$ to $E_3$ are represented by way of example in this image, which are correlated with the connected CT images $CT_1$ to $CT_3$.

By way of amplification, it should be mentioned in this connection that the video recording system of course has a display 8, on which the appropriate information from the box 10 can be displayed. A memory 9 is moreover provided, which stores the collected images.

It is therefore possible to place an exact position of a patent into correlation by means of the storing of video images and possibly location-specific diagnostic information connected therewith, such as CT images or MRIs, for example. If these images are stored so they can be called up, there is the possibility at all times of repositioning the patient in the corresponding position in the course of a repeated examination. In the same way, the information, CT images, reference images, position data, possibly camera settings, represented in the information box 10 can be output by means of the transmitting device 17 and transmitted, for example, to another system. An Internet connection or other connection to a telecommunications connection or a network is also a transmitting device herein.

Figure 3:
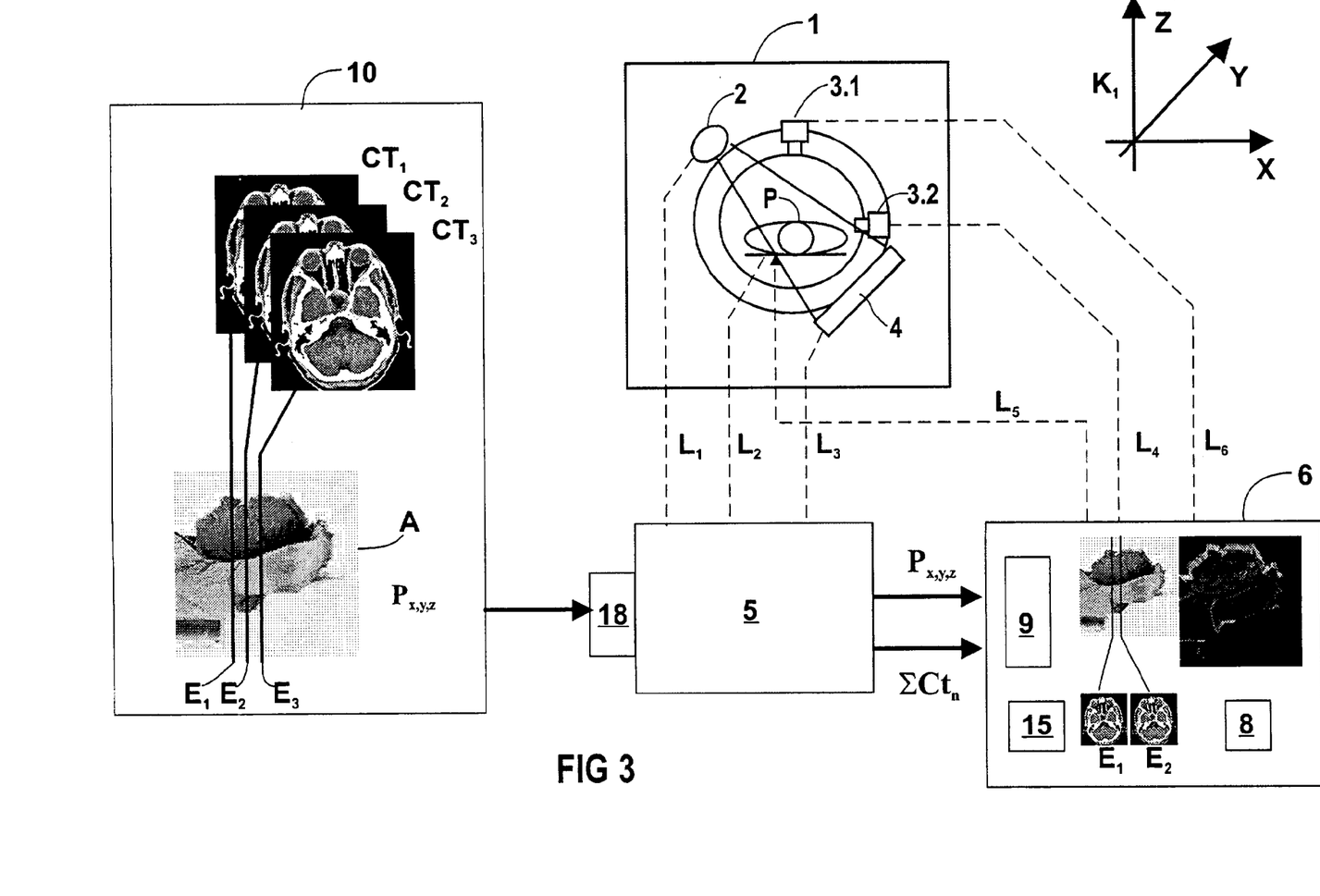
FIG. 3 is a schematic representation of a repositioning process in a CT.

Such repositioning is represented in FIG. 3. A CT with an X-ray tube 2, detector 4 and two video cameras 3.1 and 3.2 is represented there, which are arranged identically with the CT in FIG. 2. The entire image and position information obtained in a first session in the CT from FIG. 2, represented by the box 10, is made available to the CT in FIG. 3 via a receiving device 18. Now the operators have the opportunity to compare in the video recording system 6 the current images B produced by the cameras 3.1 and 3.2 with the corresponding reference images A made during a previous session, and to have the result of this comparison displayed on a monitor 8 by means of a subtraction image C known from FIG. 1. It is thereupon possible to perform an appropriate position correction, represented by the connection $L_6$, until an identical positioning of the patient P is again achieved. Thereafter, comparative CT recordings can again be prepared, which can now be compared in a considerably more accurate manner, i.e. up to a location accuracy of 1 to 2 mm, than with previous CT tomograms. A substantially more accurate course diagnosis than was possible with the prior art results in this way. A computer 15 is a component of the video recording system 6, or is at least available to it as a computing aid.

Figure 4:
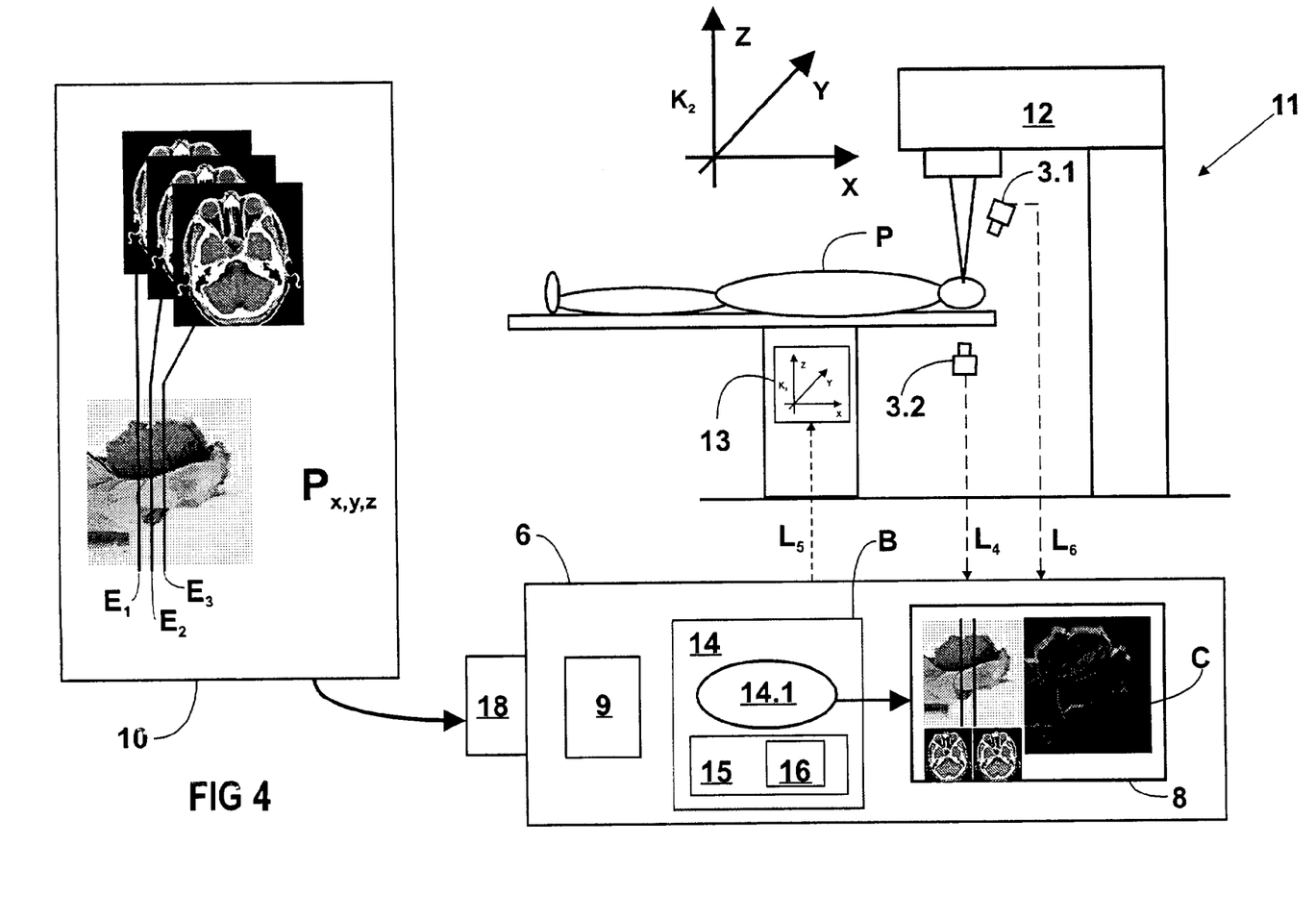
FIG. 4 shows the repositioning of a patient in a radiation-therapeutic system.

A further employment option of the positioning method is represented in FIG. 4. A radiation therapy system 11 with a radiation source 12 is represented there, by means of which a patient P can be provided with the treatment of a tumor in the head or other areas of the body, for example. In connection with such therapies, it is essential that the effects of the radiation be manifested as accurately as possible in the area of the tumor, while surrounding and healthy areas should not be affected, since with too great a radiation stress these healthy areas can be exited to form carcinomas, or could be damaged in other undesirable ways. It is therefore essential to know the exact position of a tumor in an observed area, so that the radiation therapy can be employed in an accurately aimed manner.

The radiation therapy system 11 contains the image and position information from original reference recordings provided, for example by the CT in FIG. 1. As previously explained, by performing an image comparison and producing a difference image C, which can be observed on the monitor 8, it is now possible to correct the position of the patient P in the coordinate system $K_2$ of the radiation therapy system 11 until the position of the patient P in this coordinate system $K_2$ matches the original position of the patient P in the coordinate system $K_1$ of the CT system. As previously explained, this correction is performed by an image processing device 14, which has a computer system 15 with an appropriate program 16, preferably by a subtraction method 14.1, in which a difference image C between an original reference image A and a current image B is created.

By way of example, in FIG. 4, the reference image A is compared with a fresh video recording B from the camera 3.2, and the result is displayed as the difference image C on the monitor 8. Because of the strong appearance of the positional change in the difference image C, the operators can now change the position of the patient by means of the positioning device 13 until the new positioning of the patient is optimized.

Besides this manual option of the positional change on the basis of a visible image and the positional differences represented, there is also the option of an automatic positional correction in that, based on the image information, for example the sum of the differences of the image information in a difference image, the position of the patient is changed until this difference sum has been minimized.

In an overview, FIG. 5 again shows the possibilities of the method in accordance with the invention, or of the diagnostic system I and a therapeutic system II.

Figure 5:
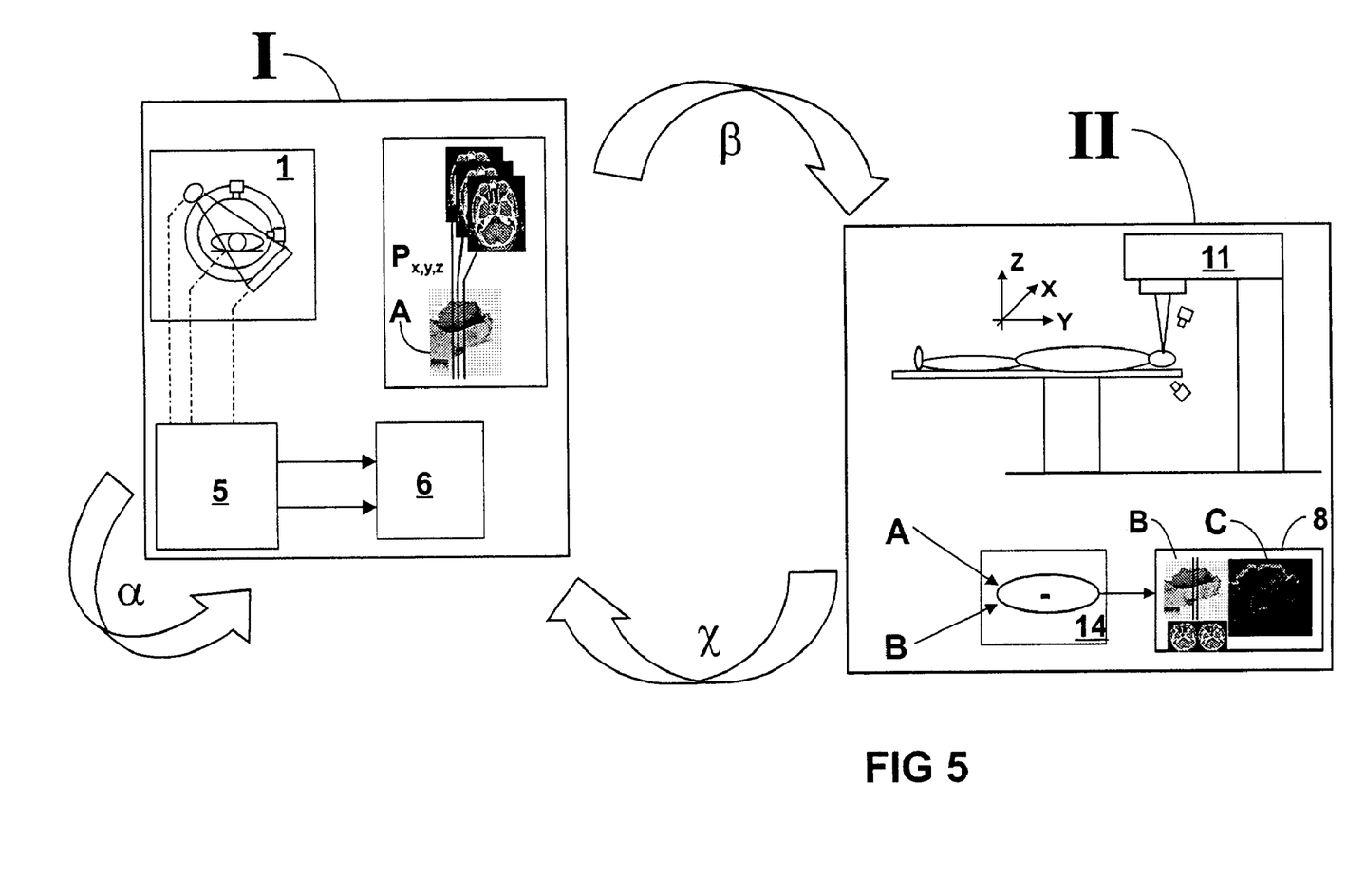
FIG. 5 is a schematic representation of the repositioning process in a computer tomograph, the process representing therapy planning with the aid of patient positioning.

The advantages of the improved repositioning within an identical, or also the same diagnostic system I are represented by the recursive arrow α. Furthermore, also the advantages regarding a more accurate therapy planning option by the arrow β from the diagnostic system I to the therapeutic system II, and finally, represented by the arrow χ, again the improved therapy success control by returning the information from the therapeutic system II to the diagnostic system I. In this connection, it should be pointed out that there is also the option of producing a first reference image for the accurate positioning of the patient in a therapeutic system, and thereafter to use this image for the subsequent positioning of the patient in the diagnostic system for therapy monitoring.

In conclusion, a method for repositioning a patient in a diagnostic/therapeutic system, as well as such a system, is represented wherein the repeated accurate repositioning is achieved by producing difference images from a reference image and a current image, each in two independent recording axes, and by minimizing the visible differences. This very simple, highly accurate repositioning possibility of a patient in an image-providing diagnostic and/or therapeutic system can also be employed in existing systems. It is merely necessary to assure that cameras are available in the exact position and setting in the desired correcting planes, whose images thereafter are processed in image processing software. The additional provision of such a system with an automatic positioning device is also possible. Therefore, a substantially improved process control, therapy planning and therapy control is made possible by means of the method of the invention.

It should be understood that the above mentioned features of the invention can be used not only in the respectively shown combination, but also in other combinations, or by themselves, without departing from the scope of the invention.

What is claimed is:

1. A method for the repeated relative positioning of a patient in an imaging diagnostic and/or radiation-therapeutic system in relation to the coordinate system of the respective system, the method comprising:

producing in a first session, at least two reference images of a patient or a part of the patient in at least two different camera positions and in different recording axes, producing current images in each subsequent session with the same camera settings, superimposing the at least two reference images with the same camera setting on at least two current images so that the differences between the images become visible, and changing thereafter the position of the patient in relation to one of the system and a diagnostic or therapeutic partial device of the system until the differences between the reference images and the current images, which are current in respect to the new position of the patient, are minimized.

2. The method in accordance with claim 1, digitally storing the previous reference images, and representing the superimposed images on a control monitor.

3. The method in accordance with claim 2, creating the superimposition of the reference images and the current images by subtraction.

4. The method in accordance with claim 1, characterized in that the superimposition of the reference images and the current images is a function of subtraction.

5. The method in accordance with claim 1, creating the superimposition of the reference images and the current images in response to two different methods.

6. The method in accordance with claim 1, extracting contours from the images prior to the superimposition of the reference images and the current images.

7. The method in accordance with claim 1,
performing an image processing prior to the superimposition of the reference images and the current images, for an improved representation of the image differences.

8. The method in accordance with claim 1,
storing in connection with at least one reference image, at least one of the position and the focus of one of the camera and recording axis in relation to the imaging diagnostic or therapeutic system, and setting up prior to producing current images, the at least one camera in accordance with the stored data.

9. The method in accordance with claim 1,
characterized in that the recording axes are independent of each other and are orthogonal to each other.

10. The method in accordance with claim 1,
producing the reference images in a first system and the current images in a second system, wherein the camera setting relative to the coordinate system of the systems are identical.

11. The method in accordance with claim 10,
characterized in that the first system is an imaging diagnostic system.

12. The method in accordance with claim 10,
characterized in that the second system is a radiation therapeutic system.

13. The method in accordance with claim 10,
bringing the reference images from the first system into spatial correlation with diagnostic tomograms from the first system, and in the second system, reestablishing the spatial correlation of the diagnostic tomograms with the current image.

14. The method in accordance with claim 10,
transmitting the reference images and the camera setting of the first system, to the second system via a remote data connection, automatically adjusting the camera of the second system in accordance with the transmitted camera settings from the first system.

15. An image-producing diagnostic and/or therapeutic system comprising:
a positioning device for the relative positioning of a patient and the system,
at least one camera for providing an image and for checking a position of a patient to be treated,
a memory device for storing the image,
a reproducing device for displaying the image,
characterized in that the following are provided:
means for producing at least two images in the visible or infrared wavelength range in at least two independent recording axes,
means for electronically storing the at least two images, and
means for comparing currently produced at least two images with reference images produced in a previous session, and
means for displaying a difference between the reference images and the at least two images.

16. The system in accordance with claim 15,
characterized in that the means for comparing the at least two images with the reference images comprises a computer system with a computer program.

17. The system in accordance with claim 15,
further comprising at least one of transmitting and receiving devices for a data net for transmitting the reference images.

18. The system in accordance with claim 15,
characterized in that the at least one camera is arranged, movably in space and/or orientation.

19. The system in accordance with claim 15,
characterized in that at least two cameras for producing the reference images and/or the at least two images are arranged with recording axes independent of each other.

20. A method for the repeated relative positioning of a patient in relation to a coordinate system of a system, the method comprising:
(a) generating a reference image of a patient in a first session with a camera at a first position;
(b) generating a current image of the patient in a second session subsequent to the first session, the current image responsive to camera settings based on the first position;
(c) comparing the reference image with the current image by performing at least one of the acts of:
(c1) displaying a combined image as a function of both the reference and current images; and
(c2) determining an off-set with a processor of the current image from the reference image; and
(d) repositioning the patient in relation to the system as a function of (c).

21. A method for positioning a patient, the method comprising:
positioning a first camera and a second camera at a known relationship to a coordinate system of an imaging or treatment apparatus, and oriented so that at least one of a visual or infra-red first image of an outer surface of a patient having a first disposition with respect to the coordinate system is obtained by each camera;
obtaining a second image of the outer surface of the patient having a second disposition with respect to the coordinate system using the first and the second camera; and
adjusting the position of the patient such that a second disposition of the patient and the first disposition of the patient are substantially identical, the method further comprising:
comparing the first image obtained by the first camera with the second image obtained by the first camera; and
comparing the first image obtained by the second camera with the second image obtained by the second camera.

22. The method of claim 21, wherein the steps of comparing comprise computing a difference between the first image and the second image obtained by each cameras, respectively.

23. A method for positioning a patient, the method comprising:
providing a first imaging or treatment apparatus having a first coordinate system and a second imaging or treatment apparatus having a second coordinate system, the coordinate systems having a known relationship to each other;
positioning a first camera and a second camera at a known relationship to the first coordinate system, and oriented so that at least one of a visual or infra-red first image of an outer surface of a patient having a first disposition is obtained by each camera;
positioning a third camera and a fourth camera at a known relationship to the second coordinate system and oriented so that at least one of a visual or infra-red first image of the outer surface of the patient having a disposition with respect to the second coordinate system is obtained by each camera;

adjusting the position of the patient or the second apparatus such that a second disposition of the patient and the first disposition of the patient are substantially identical with respect to the respective coordinate systems, the method further comprising:

comparing the image obtained by the first camera with the image obtained by the third camera; and comparing the image obtained by the second camera with the image obtained by the fourth camera.

24. The method of claim 23, wherein the first apparatus and the second apparatus are the same apparatus, the first camera and the third camera are the same camera, and the second camera and the fourth camera are the same camera.

25. The method of claim 23, wherein the comparing the image comprises computing a difference between the images obtained by the first camera and the third camera, and computing a difference between the images obtained by the third camera and the fourth camera.

* * * * *